(12) United States Patent
Van Gompel et al.

(10) Patent No.: US 7,344,523 B2
(45) Date of Patent: Mar. 18, 2008

(54) DUAL-LAYERED DISPOSABLE GARMENT HAVING TAILORED STRETCH CHARACTERISTICS

(75) Inventors: Paul T. Van Gompel, Hortonville, WI (US); Georgia L. Zehner, Larsen, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/749,761

(22) Filed: Dec. 31, 2003

(65) Prior Publication Data

US 2005/0148977 A1 Jul. 7, 2005

(51) Int. Cl.
*A61F 13/20* (2006.01)

(52) U.S. Cl. .......................... 604/385.22; 604/385.23; 604/385.24; 604/385.27; 604/385.29; 604/385.3

(58) Field of Classification Search ............................... 604/385.22–385.3, 393–402
See application file for complete search history.

(56) References Cited

U.S. PATENT DOCUMENTS

| | | | |
|---|---|---|---|
| 2,931,361 A | 4/1960 | Sostrin | |
| 3,849,241 A | 11/1974 | Butin et al. | |
| 3,978,861 A | 9/1976 | Schaar | |
| 4,036,233 A | 7/1977 | Kozak | |
| 4,050,462 A | 9/1977 | Woon et al. | |
| 4,100,324 A | 7/1978 | Anderson et al. | |
| 4,205,679 A | 6/1980 | Repke et al. | |
| 4,560,372 A | 12/1985 | Pieniak | |
| 4,573,986 A | 3/1986 | Minetola et al. | |
| 4,631,062 A | 12/1986 | Lassen et al. | |
| 4,657,802 A | 4/1987 | Morman | |
| 4,663,220 A | 5/1987 | Wisneski et al. | |
| 4,699,622 A | 10/1987 | Toussant et al. | |
| 4,704,114 A | 11/1987 | Wilson et al. | |
| 4,704,116 A | 11/1987 | Enloe | |
| 4,710,187 A | 12/1987 | Boland et al. | |
| 4,720,415 A | 1/1988 | Vander Wielen et al. | |

(Continued)

FOREIGN PATENT DOCUMENTS

EP 0 217 032 A2 4/1987

(Continued)

OTHER PUBLICATIONS

"Polyethylene—Low Density (LDPE)—Material Information," Internet web page "http://www.goodfellow.com/csp/active/STATIC/E/Polyethylene_-_Low_Density.HTML", p. 3, line 1, Goodfellow Corporation, Devon, PA.

Primary Examiner—Tatyana Zalukaeva
Assistant Examiner—Ginger Chapman
(74) Attorney, Agent, or Firm—Alyssa Dudkowski; David J. Arteman (57) ABSTRACT

The present invention relates to improvements in structure of disposable garments. The disposable garments of the invention may include an outer layer and an elastic inner layer. The elastic inner layer has an elastic inner layer perimeter and defines an opening, which may be in the form of a slit or aperture, located in an internal position to the elastic inner layer perimeter. The elastic inner layer perimeter may be bonded to the outer layer. The elastic inner layer may include a front piece, a back piece and a crotch piece.

16 Claims, 7 Drawing Sheets

U.S. PATENT DOCUMENTS

| | | | | |
|---|---|---|---|---|
| 4,731,066 A | * | 3/1988 | Korpman | 604/366 |
| 4,747,846 A | | 5/1988 | Boland et al. | |
| 4,752,349 A | | 6/1988 | Gebel | |
| 4,753,646 A | | 6/1988 | Enloe | |
| 4,756,709 A | * | 7/1988 | Stevens | 604/385.22 |
| 4,808,176 A | | 2/1989 | Kielpikowski | |
| 4,834,736 A | | 5/1989 | Boland et al. | |
| 4,846,823 A | | 7/1989 | Enloe | |
| 4,850,992 A | | 7/1989 | Amaral et al. | |
| 4,854,995 A | | 8/1989 | Kasper et al. | |
| 4,865,597 A | | 9/1989 | Mason et al. | |
| 4,869,724 A | | 9/1989 | Scripps | |
| 4,874,451 A | | 10/1989 | Boger et al. | |
| 4,892,536 A | | 1/1990 | Desmarais et al. | |
| 4,895,569 A | | 1/1990 | Wilson et al. | |
| 4,935,021 A | | 6/1990 | Huffman et al. | |
| 4,936,840 A | | 6/1990 | Proxmire | |
| 4,938,755 A | | 7/1990 | Foreman | |
| 4,940,464 A | | 7/1990 | Van Gompel et al. | |
| 4,988,346 A | | 1/1991 | Pfefferkorn | |
| 4,990,147 A | * | 2/1991 | Freeland | 604/385.22 |
| 5,026,364 A | | 6/1991 | Robertson | |
| 5,037,416 A | * | 8/1991 | Allen et al. | 604/385.22 |
| 5,046,272 A | | 9/1991 | Vogt et al. | |
| 5,104,116 A | | 4/1992 | Pohjola | |
| 5,114,781 A | | 5/1992 | Morman | |
| 5,116,662 A | | 5/1992 | Morman | |
| 5,151,092 A | | 9/1992 | Buell et al. | |
| 5,224,405 A | | 7/1993 | Pohjola | |
| 5,226,992 A | | 7/1993 | Morman | |
| 5,242,436 A | | 9/1993 | Weil et al. | |
| 5,269,775 A | * | 12/1993 | Freeland et al. | 604/385.22 |
| 5,284,703 A | | 2/1994 | Everhart et al. | |
| 5,340,424 A | | 8/1994 | Matsushita | |
| 5,350,624 A | | 9/1994 | Georger et al. | |
| 5,356,405 A | | 10/1994 | Thompson et al. | |
| 5,368,584 A | | 11/1994 | Clear et al. | |
| 5,397,316 A | | 3/1995 | Lavon et al. | |
| 5,397,317 A | | 3/1995 | Thomas | |
| 5,462,537 A | | 10/1995 | Carr et al. | |
| 5,486,166 A | | 1/1996 | Bishop et al. | |
| 5,490,846 A | | 2/1996 | Ellis et al. | |
| 5,503,076 A | | 4/1996 | Yeo | |
| 5,503,919 A | | 4/1996 | Litchholt et al. | |
| 5,554,143 A | | 9/1996 | Roe et al. | |
| 5,611,790 A | | 3/1997 | Osborn et al. | |
| 5,624,422 A | | 4/1997 | Allen | |
| 5,634,916 A | | 6/1997 | Lavon et al. | |
| 5,643,242 A | | 7/1997 | Lavon et al. | |
| 5,645,542 A | | 7/1997 | Anjur et al. | |
| 5,658,269 A | | 8/1997 | Osborn et al. | |
| 5,681,302 A | | 10/1997 | Melbye et al. | |
| 5,690,627 A | | 11/1997 | Clear et al. | |
| 5,695,868 A | | 12/1997 | Mccormack | |
| 5,766,389 A | | 6/1998 | Brandon et al. | |
| 5,779,690 A | | 7/1998 | Gustafsson et al. | |
| 5,797,896 A | | 8/1998 | Schmitz | |
| 5,804,021 A | | 9/1998 | Abuto et al. | |
| 5,817,086 A | * | 10/1998 | Kling | 604/385.19 |
| 5,820,973 A | | 10/1998 | Dodge, II et al. | |
| 5,843,056 A | | 12/1998 | Good et al. | |
| 5,846,232 A | | 12/1998 | Serbiak et al. | |
| 5,873,868 A | | 2/1999 | Nakahata | |
| 5,883,028 A | | 3/1999 | Morman et al. | |
| 5,928,211 A | | 7/1999 | Gustafsson et al. | |
| 5,947,947 A | | 9/1999 | Tanzer et al. | |
| 5,957,907 A | | 9/1999 | Sauer | |
| 5,964,743 A | | 10/1999 | Abuto et al. | |
| 5,997,981 A | | 12/1999 | Mccormack et al. | |
| 6,049,915 A | | 4/2000 | Malowaniec | |
| 6,093,870 A | | 7/2000 | Carlsson | |
| 6,103,953 A | | 8/2000 | Cree et al. | |
| 6,120,485 A | * | 9/2000 | Gustafsson et al. | 604/385.19 |
| 6,129,720 A | * | 10/2000 | Blenke et al. | 604/385.16 |
| 6,132,410 A | | 10/2000 | Van Gompel et al. | |
| 6,132,411 A | | 10/2000 | Huber et al. | |
| 6,149,638 A | | 11/2000 | Vogt et al. | |
| 6,149,934 A | | 11/2000 | Krzysik et al. | |
| 6,160,197 A | | 12/2000 | Lassen et al. | |
| 6,174,303 B1 | | 1/2001 | Suprise et al. | |
| 6,193,701 B1 | | 2/2001 | Van Gompel et al. | |
| 6,217,563 B1 | | 4/2001 | Van Gompel et al. | |
| 6,231,557 B1 | | 5/2001 | Krautkramer et al. | |
| 6,262,331 B1 | | 7/2001 | Nakahata et al. | |
| 6,264,639 B1 | | 7/2001 | Sauer | |
| 6,264,641 B1 | | 7/2001 | Van Gompel et al. | |
| 6,312,786 B1 | | 11/2001 | Schwinn | |
| 6,362,389 B1 | | 3/2002 | McDowall et al. | |
| 6,409,711 B1 | | 6/2002 | Jönbrink | |
| 6,413,247 B1 | | 7/2002 | Carlucci et al. | |
| 6,461,338 B1 | | 10/2002 | Shimoe et al. | |
| 6,482,191 B1 | * | 11/2002 | Roe et al. | 604/385.01 |
| 6,521,811 B1 | | 2/2003 | Lassen et al. | |
| 6,547,774 B2 | * | 4/2003 | Ono et al. | 604/385.29 |
| 6,552,245 B1 | | 4/2003 | Roessler et al. | |
| 6,570,056 B1 | | 5/2003 | Tanzer et al. | |
| 6,572,598 B1 | | 6/2003 | Ashton et al. | |
| 6,582,414 B1 | | 6/2003 | Richardson | |
| 6,610,383 B1 | | 8/2003 | Morman et al. | |
| 6,623,465 B1 | | 9/2003 | Roe et al. | |
| 6,632,212 B1 | | 10/2003 | Morman et al. | |
| 6,645,190 B1 | | 11/2003 | Olson et al. | |
| 6,679,869 B1 | * | 1/2004 | Schlinz et al. | 604/385.22 |
| 6,682,512 B2 | | 1/2004 | Uitenbroek et al. | |
| 6,702,799 B2 | | 3/2004 | Otsubo | |
| 6,702,800 B1 | | 3/2004 | Vukos et al. | |
| 6,703,538 B2 | | 3/2004 | Lassen et al. | |
| 6,706,028 B2 | | 3/2004 | Roe et al. | |
| 6,755,808 B2 | | 6/2004 | Balogh et al. | |
| 6,913,599 B2 | * | 7/2005 | Mishima et al. | 604/385.08 |
| 6,969,378 B1 | | 11/2005 | Vukos et al. | |
| 2002/0013563 A1 | | 1/2002 | Lassen et al. | |
| 2002/0029029 A1 | | 3/2002 | Otsubo | |
| 2002/0072726 A1 | | 6/2002 | Mishima et al. | |
| 2002/0104608 A1 | | 8/2002 | Welch et al. | |
| 2002/0111598 A1 | | 8/2002 | Vogt et al. | |
| 2002/0165516 A1 | | 11/2002 | Datta et al. | |
| 2002/0169432 A1 | | 11/2002 | Fell et al. | |
| 2003/0023213 A1 | | 1/2003 | Fernfors et al. | |
| 2003/0088230 A1 | | 5/2003 | Balogh et al. | |
| 2003/0125696 A1 | | 7/2003 | Morman et al. | |
| 2004/0013850 A1 | | 1/2004 | Kling | |
| 2004/0044323 A1 | | 3/2004 | Roessler et al. | |
| 2004/0102749 A1 | | 5/2004 | Olson et al. | |
| 2004/0127878 A1 | | 7/2004 | Olson et al. | |
| 2004/0127881 A1 | | 7/2004 | Stevens et al. | |
| 2005/0043460 A1 | | 2/2005 | McCormack et al. | |
| 2005/0143710 A1 | * | 6/2005 | Van Gompel et al. | 604/393 |
| 2005/0148975 A1 | * | 7/2005 | Van Gompel et al. | 604/385.01 |
| 2005/0148976 A1 | * | 7/2005 | Van Gompel et al. | 604/385.01 |
| 2005/0148982 A1 | * | 7/2005 | Van Gompel et al. | 604/385.22 |
| 2005/0148987 A1 | * | 7/2005 | Van Gompel et al. | 604/393 |

FOREIGN PATENT DOCUMENTS

| | | |
|---|---|---|
| EP | 0 835 088 B1 | 2/2000 |
| EP | 1 201 212 A2 | 5/2002 |
| EP | 0 957 868 B1 | 2/2003 |
| GB | 2 284 538 A | 6/1995 |
| GB | 2 305 610 A | 4/1997 |
| GB | 2 310 606 A | 9/1997 |
| GB | 2 325 146 A | 11/1998 |
| JP | 60-194947 A | 10/1985 |
| WO | WO 93/06805 A1 | 4/1993 |

| | | |
|---|---|---|
| WO | WO 95/15410 A1 | 6/1995 |
| WO | WO 95/19753 A1 | 7/1995 |
| WO | WO 98/29239 A1 | 7/1998 |
| WO | WO 98/52506 A1 | 11/1998 |
| WO | WO 99/33426 A1 | 7/1999 |
| WO | WO 99/33427 A1 | 7/1999 |
| WO | WO 00/37009 A2 | 6/2000 |
| WO | WO 01/88245 A2 | 11/2001 |
| WO | WO 02/34184 A1 | 5/2002 |
| WO | WO 02/069870 A2 | 9/2002 |
| WO | WO 03/057106 A1 | 7/2003 |
| WO | WO 2004/108041 A1 | 12/2004 |

* cited by examiner

DUAL-LAYERED DISPOSABLE GARMENT HAVING TAILORED STRETCH CHARACTERISTICS

BACKGROUND OF THE INVENTION

Disposable garments, including disposable absorbent garments, have been known for decades. Disposable garments may include garments worn like underpants for children and adults, garments worn like training pants for toddlers and garments worn like diapers for infants. Disposable absorbent garments designed to absorb and contain bodily fluids may include adult/child incontinence garments, toddler training pants and infant diapers. "Disposable" is generally understood to mean something that has a limited period of use before its ability to perform its intended function is exhausted. With regard to garments, "disposable" garments typically are not constructed to withstand laundering.

Typically, it is desirable for disposable garments to fit close to the body of the wearer for comfort and discretion. The disposable garment may have or form an opening that fits around the user's waist, as well as two openings that fit around the user's legs. The disposable garment typically includes a front waist region, a back waist region and a crotch region that extends between and connects the front and back waist regions. The front waist region includes the portion of the disposable garment that, when worn, is positioned on the front of the user while the back waist region includes the portion of the disposable garment that, when worn, is positioned on the back of the user. The crotch region of the disposable garment includes the portion of the disposable garment that, when worn, is positioned between the legs of the user and covers the lower torso of the user. Disposable garments may include one or more layers of materials, such as nonwoven materials. For example, a disposable garment may include a liner material that forms the layer of material closest to the user's skin and an outer material that forms the layer of material closest to the user's other clothing. Disposable garments may also include features that improve how well the garments fit the user. For example, disposable garments may include stretchable, such as elastic, materials near the waist opening and leg openings of the garment to improve the fit of the garment around the user's waist and legs. Additionally, disposable garments may include fasteners that assist with securing the position of the garment in use. For example, disposable garments may include adhesive or mechanical fasteners to assist with securing the garments around the waists of the users. Disposable garments may include additional features that improve the fit range (i.e. the range of users able to wear a particular size of absorbent garment) of the garments.

Disposable absorbent garments may be similar to disposable garments and provide the ability to absorb and contain bodily fluids such as urine, feces and menses. In addition to one or more layers of materials similar to disposable garments, disposable absorbent garments may also include an absorbent material. For example, if a disposable absorbent garment includes a single layer of material, the absorbent material may be located on the side of the single layer of material that will be positioned closest to the user's skin during wear. A representative example of a commonly used disposable absorbent garment is a disposable diaper to be used by an infant or toddler. Disposable diapers may have various shapes when they are open or unfastened and laying generally flat. For example, disposable diapers may have an overall rectangular shape, T-shape, I-shape or hourglass shape. Disposable absorbent garments, such as infant diapers, have a longitudinal direction that generally corresponds to the length of the garments and a lateral direction that generally corresponds to the width of the garments. Disposable absorbent garments typically include at least four edges: a pair of laterally opposed side edges and a pair of longitudinally opposed waist edges. Disposable absorbent garments may include an interior surface that is configured to contact the user's skin during wear and an exterior surface opposite the interior surface that is configured to contact the user's clothing during wear.

Presently available disposable diapers include at least three layers: a substantially liquid impermeable outer cover (a.k.a. a "backsheet"), a liquid permeable bodyside liner (a.k.a. a "topsheet") that can be connected to the outer cover in a superposed relation and an absorbent core (or absorbent "body") that is located between the outer cover and the bodyside liner. The side edges of the outer cover generally define the laterally opposed side edges of the disposable diaper and the side edges may form curvilinear leg openings when the disposable diaper is worn. The waist edges of the outer cover generally define the waist edges of the disposable diaper and typically form the waist opening that is configured to encircle the waist of the user when the disposable absorbent garment is worn. The absorbent core is configured to contain and/or absorb body exudates discharged from the user. Presently-available disposable diapers typically include waist elastics, leg elastics and containment flaps. Presently-available disposable diapers further include adhesive tape fasteners or refastenable mechanical fasteners (or combinations of both) for releasably engaging the opposed side edges of the disposable diaper in the opposite waist regions. The mechanical fasteners can include a variety of materials and surfaces known for mechanical engagement such as buttons, pins, snaps, cohesives, mushroom-and-loop fasteners and hook and loop fasteners. Many disposable diapers also include an attachment panel located on the front or back waist region, opposite the fasteners to which the fasteners can be releasably engaged while the disposable diaper is worn.

While disposable garments and disposable absorbent garments have been known for many years, the materials used to construct them have continuously evolved as a result of new technologies for formulating and manufacturing disposable materials. Materials may be selected for performance or to provide a cost advantage, particularly given that many manufacturers produce disposable garments and disposable absorbent garments in very large quantities. One aspect of evolution has been the development and availability of stretchable materials to replace previously non-stretchable components in order to provide improvements in the way in which the garments fit and improvements in the range of fit of the garments. An example of a stretchable material for use in disposable garments is a necked bonded laminate material (hereinafter "NBL material"). One of the first uses identified for a stretchable material, such as a NBL material, in the construction of a disposable diaper was as an "ear" material where the "ear" was attached to the longitudinal side edge of the diaper in the back waist region and to which was attached a mechanical fastener engageable with the front waist region.

Stretchable materials may include materials that are extensible and materials that are elastic. "Extensible" materials typically have lower capacities to retract to their original lengths after stretching while "elastic" materials typically have a greater range of stretch and come close to completely retracting to their original lengths after stretching. Presently-available disposable diapers, including HUG- GIES Supreme diapers manufactured by Kimberly-Clark Corporation, are constructed with an extensible outer cover material and an extensible bodyside liner material.

With the advent of the availability of stretchable materials to construct disposable absorbent garments, various configurations for garments incorporating stretchable materials have been described. For example, once a stretchable material is selected to form a component of a garment, the material may be modified to provide a range of stretch characteristics. International Publication No. WO 99/33427 (hereinafter "the 33427 publication") describes personal care articles that may include resiliently stretchable outer covers and/or resiliently stretchable bodyside liners. The 33427 publication describes that the resiliently stretchable materials may be "embossed" to modify the "resistance to stretch" properties. The "embossments" may be used to reduce or otherwise control the stretching of different portions or "zones" of the garments. Therefore, in addition to stretchable materials themselves being available for use in absorbent garments, the potential for some forms of modification of the stretch properties has also been described.

In addition to garments utilizing extensible and otherwise stretchable materials, garments utilizing elastic materials have been described. International Publication No. WO 02/34184 (hereinafter "the 34184 publication") describes absorbent garments that may have a biaxially stretchable outer cover and a biaxially stretchable bodyside liner. The "biaxially stretchable" materials described as being suitable in the 34184 publication include elastic materials capable of stretching in at least two directions.

Simultaneous with the development of stretchable materials having lower cost and/or improved properties for use in disposable garments, developments with regard to the structural features of disposable garments have also occurred. Just as stretchable ears were developed to improve the fit of garments, other features have been developed to improve the waste containment function of the garments. An example of one such class of features is the provision of holes or apertures between layers of the garments to separate the waste materials from the wearer's skin. More specific examples of such features are apertures or openings in the bodyside liners of disposable absorbent garments that are provided to separate solid wastes from the wearer's skin to reduce the incidence of troublesome conditions such as diaper rash. In addition to skin health benefits, the ease of cleaning may be improved when the garment is designed to isolate wastes from the skin of the wearer. Apertures or opening in the bodyside liner have been described along with other features of the bodyside liner, such as a bodyside liner having multiple sections. U.S. Pat. No. 5,269,775 to Freeland et al. (hereinafter "the Freeland patent") describes topsheets divided into three trisections: a front trisection, a central trisection, and a rear trisection. The front trisection has no elastic extensibility, the central trisection is transversely elastically extensible and the rear trisection is longitudinally elastically extensible. The Freeland patent states that the topsheet may be provided with an aperture for communicating fecal material through the topsheet. The longitudinally elastically extensible rear trisection is described as providing close conformance of the topsheet to the buttocks of the wearer. The transverse contraction of the crotch portion is described as providing shaping of the article. The arrangement of the front trisection being provided without any elastic extensibility is described as conforming less closely to the wearer to more comfortably accommodate the genitalia of the wearer.

Even though significant and numerous advancements have occurred in the materials and structural features available for the construction of disposable garments, there remain opportunities for improvement in the fit and containment capacity of such garments. For example, there remains a need for a disposable garment that provides excellent fit on the wearer that results in reduced leakage and that provides a barrier between the wearer's skin and the waste materials being contained by the garment. Additionally, there remains a need for a disposable garment that has a simplified construction and that eliminates the attachment of multiple separate components that increase the cost and complicate the manufacture of disposable garments.

SUMMARY OF THE INVENTION

The present invention relates generally to disposable garments and to disposable absorbent garments. The disposable garments may include an outer layer and an elastic inner layer. The elastic inner layer may include an elastic inner layer perimeter and the elastic inner layer perimeter may be bonded to the outer layer. The elastic inner layer may include a front piece, a back piece and a crotch piece. The crotch piece may be attached to the front piece and the back piece. The front piece and the back piece may be elastic in a lateral direction of the disposable garment. The lateral direction generally corresponds to the width of the garment. The crotch piece may be elastic in a longitudinal direction of the disposable garment. The longitudinal direction generally corresponds to the length of the garment and is generally perpendicular to the width of the garment. The crotch piece may define an opening that is located in an internal position to the elastic inner layer perimeter. The opening may be either a slit or an aperture. Additionally, the outer layer may have an outer layer perimeter. The elastic inner layer perimeter may be bonded to the outer layer perimeter. The elastic inner layer perimeter and the outer layer perimeter are defined by the outer edges or boundaries of the elastic inner layer and the outer layer.

The outer layer may be formed from a material that is extensible. Extensible materials are generally understood to be materials that are capable of stretching in one or more directions but that do not fully retract to their original length when a pulling force is released. For example, the outer layer may be formed of a material that is extensible in the lateral direction of the garment. The outer layer may also be formed from a material that is elastic. Elastic materials are generally understood to be materials that are stretchable in one or more directions and that are capable of retracting to substantially their original length when a pulling force is released. The outer layer may be formed from a material that is either liquid impermeable or liquid permeable. When the outer layer is formed from a liquid impermeable material, the outer layer may act as a barrier. The outer layer may be formed in such a way as to include one or more pleats. The pleats may provide the capacity for the outer layer to expand in either the lateral direction or the longitudinal direction.

The elastic inner layer may be formed from two or more layers of materials. Additionally, the elastic inner layer may be formed from a material that is liquid impermeable. The opening that is formed within the elastic inner layer may have a length that is from about 10 percent to about 80 percent of the total length of the disposable garment. The elastic inner layer perimeter may be bonded to the outer layer by a plurality of ultrasonic, adhesive or thermal bonds.

In some aspects, it may be desirable for the outer layer to be larger than the elastic inner layer. For example, the outer layer may have a length in the longitudinal direction that is greater than the length of the elastic inner layer. Alternatively, the outer layer may have a width in the lateral direction of the disposable garment that is greater than the width of the elastic inner layer. It is possible for both the length and the width of the outer layer to be greater than the length and the width of the elastic inner layer. When the elastic inner layer is bonded to the outer layer, the region in which the two components are bonded together may define a perimeter bonded area. The disposable garment may have a longitudinal side edge that includes the perimeter bonded area. The perimeter bonded area may have a percentage of bonded area to unbonded area of from about 10 percent to about 40 percent. The bonded area represents the cumulative area of the individual bond points.

In another aspect, the present invention relates to a disposable garment having a longitudinal direction and a lateral direction. The disposable garment may also include an outer layer and an elastic inner layer. The outer layer may have an outer layer perimeter and may be formed from a liquid impermeable material. The elastic inner layer may have an elastic inner layer perimeter. The elastic inner layer perimeter may be bonded to the outer layer perimeter by a plurality of ultrasonic bonds. The elastic inner layer may include a front piece, a back piece and a crotch piece. The crotch piece may be attached to the front piece and the back piece. The front piece and the back piece may be elastic in the lateral direction of the garment and the crotch piece may be elastically stretchable in the longitudinal direction of the garment. The crotch piece may define an opening that is located in a position internal to the elastic inner layer perimeter. The opening may have a length of from about 10 percent to about 80 percent of the total length of the disposable garment. The disposable garment may have a longitudinal side edge that includes the perimeter bonded area where the elastic inner layer is bonded to the outer layer. The perimeter bonded area may have a percentage of bonded area to unbonded area of from about 20 percent to about 40 percent.

In another aspect, the present invention relates to a disposable garment including a stretchable outer layer and an elastic inner layer. The elastic inner layer may have an elastic inner layer perimeter and the elastic inner layer perimeter may be bonded to the stretchable outer layer. The elastic inner layer may include a front piece, a back piece and a crotch piece. The crotch piece may be attached to the front piece and the back piece. The front piece and the back piece may be elastic in a lateral direction of the disposable garment and the crotch piece may be elastic in a longitudinal direction of the disposable garment. The crotch piece may also be extensible in the lateral direction of the disposable garment. However, it is possible for the pieces of the elastic inner layer to have different combinations of stretch characteristics. For example, the crotch piece may have a crotch piece retraction value that is greater than the retraction value of the stretchable outer layer. Further, the crotch piece may define an opening that is located in an internal position to the elastic inner layer perimeter.

In yet another aspect, the present invention relates to a disposable absorbent garment. The disposable absorbent garment may include an outer layer, an elastic inner layer and an absorbent assembly positioned between the outer layer and the elastic inner layer. The elastic inner layer may include an elastic inner layer perimeter. The elastic inner layer perimeter may be bonded to the outer layer. The elastic inner layer may include a front piece, a back piece and a crotch piece. The crotch piece may be attached to the front piece and the back piece. The front piece and the back piece may be elastically stretchable in a lateral direction of the disposable absorbent garment. At the same time, the crotch piece may be elastically stretchable in the longitudinal direction of the disposable absorbent garment. The crotch piece may define an opening that is located in an internal position to the elastic inner layer perimeter. The absorbent assembly may include a topsheet layer, a core layer and a barrier layer. The absorbent assembly may be attached to the outer layer along a line that is located along a lateral centerline. The lateral centerline is an imaginary line that runs along the length of the disposable absorbent garment and divides the garment in approximately in half in the lateral direction.

These aspects and additional aspects of the invention will be described in greater detail herein. Further, it is to be understood that both the foregoing general description and the following detailed description are exemplary and are intended to provide further explanation of the invention claimed. The accompanying drawings, that are incorporated in and constitute part of this specification, are included to illustrate and provide a further understanding of the disposable absorbent articles of the invention. Together with the description, the drawings serve to explain various aspects of the invention.

BRIEF DESCRIPTION OF THE DRAWINGS

The present invention will be more fully understood and further advantages will become apparent when reference is made to the following detailed description of the invention and the accompanying drawings wherein like numerals represent like elements. The drawings are merely representative and are not intended to limit the scope of the appended claims.

DETAILED DESCRIPTION OF THE INVENTION

The present disclosure of the invention will be expressed in terms of its various components, elements, constructions, configurations, arrangements and other features that may also be individually or collectively be referenced by the term, "aspect(s)" of the invention, or other similar terms. It is contemplated that the various forms of the disclosed invention may incorporate one or more of its various features and aspects, and that such features and aspects may be employed in any desired, operative combination thereof.

It should also be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The present invention is directed to solving problems related to providing disposable garments having close-to-the-body fit with low leakage of bodily fluids; providing disposable garments that have a barrier between the wearer's skin and bodily fluids; and providing disposable garments that have a simplified construction with a minimal number of separate components that need to be attached to the garments. Additionally, the present invention is directed to a garment having a unique combination of features that provide previously unrecognized and unexpected benefits, as will be described herein. This detailed description of the present invention will include a description of a representative disposable garment including the various components of such garments. The description of the representative disposable garment will also include a description of the features encompassed by the present invention.

Representative Disposable Garment

The disposable garments of the present invention will be described in terms of a disposable garment that is adapted to be worn by infants about the lower torso, that is, a disposable garment that is similar to a disposable diaper. It is understood that the features of the present invention are equally adaptable for other types of disposable garments such as adult incontinence garments, training pants, disposable swim pants and feminine hygiene garments.

Figure 1:
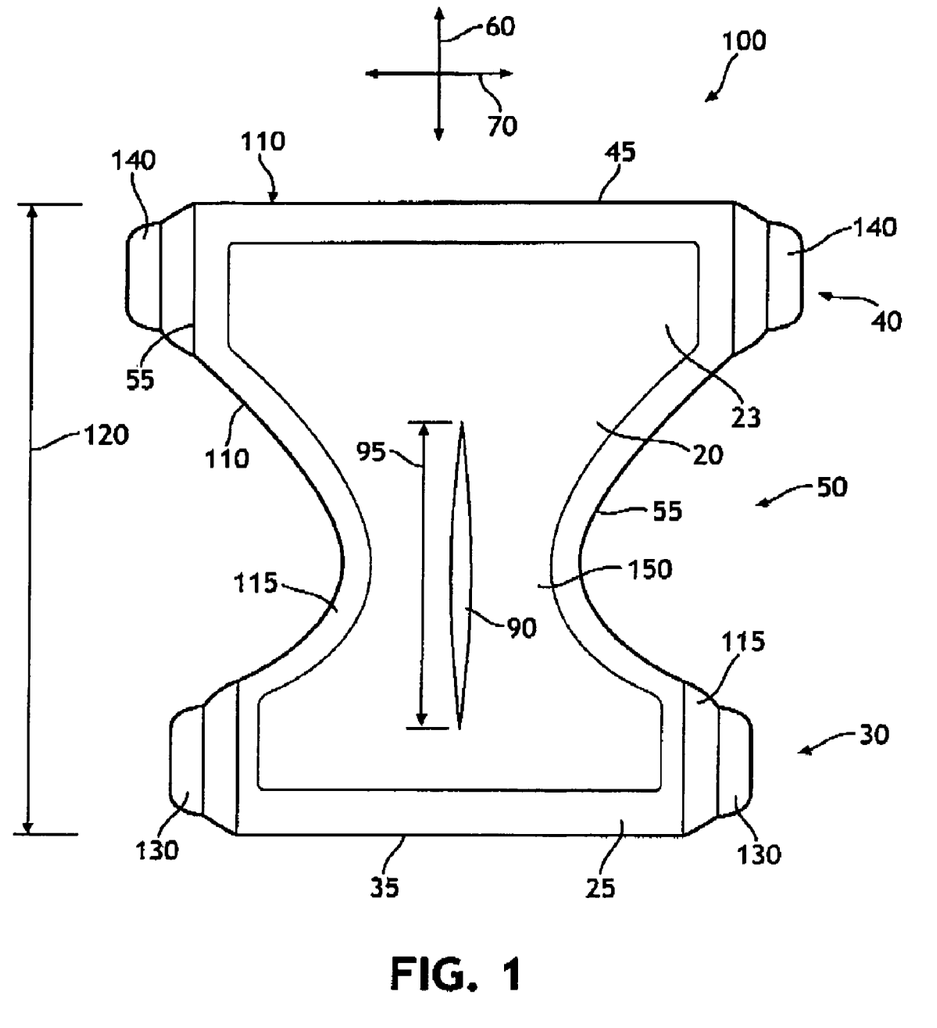
FIG. 1 representatively shows a plan view of an example of a disposable garment of the present invention (a garment to be worn by an infant/toddler) in an unfastened and laid flat condition with the surface of the garment that contacts the wearer's skin facing the viewer.

FIG. 1 representatively illustrates a disposable garment of the invention in a flat, laid-out configuration, as generally indicated at 100. The disposable garment 100 may include an outer layer (not visible in FIG. 1) and an elastic inner layer 20. The disposable garment 100 generally defines a front waist region 30, a back waist region 40 and a crotch region 50 in between the front waist region 30 and the back waist region 40. The disposable garment 100 has a longitudinal direction 60 aligned with the length 120 of the disposable garment 100 and a lateral direction 70 aligned with the width of the disposable garment 100. The lateral direction 70 is generally perpendicular to the longitudinal direction 60.

The elastic inner layer 20 includes an elastic material so that the elastic inner layer 20 is elastically stretchable in the longitudinal direction 60, the lateral direction 70 or both the longitudinal direction 60 and the lateral direction 70. The elastic inner layer 20 is elastically stretchable in such a way that the material is capable of substantially returning to its original length after removal of a pulling force. The outer layer 80 (visible in FIG. 2) may be formed of a stretchable material such that the outer layer 80 is extensible or elastic. When the outer layer 80 is formed of an extensible material, the outer layer 80 is capable of extending in the longitudinal direction 60, the lateral direction 70 or both the longitudinal direction 60 and the lateral direction 70. As will be described in further detail herein, extensible materials are capable of stretching but do not substantially return to their original length when the pulling force is removed. Instead, extensible materials experience some degree of permanent deformation from their original length. As with the elastic inner layer 20, when the outer layer 80 is formed of an elastic material, the outer layer 80 is capable of elastically stretching in the longitudinal direction 60, the lateral direction 70 or both the longitudinal direction 60 and the lateral direction 70.

Various materials may be provided for the elastic inner layer 20 and the outer layer 80, when it is desirable for the outer layer 80 to be constructed from elastic materials. For example, various nonwoven materials are known that may be elastically stretchable in a machine direction (typically, the same as the longitudinal direction 60 of the garment 100) or a cross direction (which may be the same as the lateral direction 70 of the garment 100), or both. Suitable nonwoven materials include elastic nonwoven materials and laminates of nonwoven and elastic materials. The elastic inner layer 20 and the outer layer 80 may also be formed from elastically stretchable film materials. Exemplary elastic films that are breathable are described in U.S. patent application Ser. No. 10/703,761 filed on Nov. 7, 2003 and titled "Microporous Breathable Elastic Films, Methods of Making Same, And Limited Use or Disposable Product Applications", the disclosure of which is hereby incorporated by reference. Use of such breathable, elastic films may provide additional benefits for the skin health of the wearers of the garments of the invention.

Suitable elastic nonwoven materials include elastomeric materials that are treated using nonwoven manufacturing processes such as meltblowing. Suitable elastomers that may be formed into microfibers/nonwoven webs are described in U.S. Pat. No. 4,663,220 issued to Wisneski et al. on May 5, 1987 and titled "Polyolefin-Containing Extrudable Compositions and Methods for Their Formulation Into Elastomeric Products Including Microfibers", the disclosure of which is hereby incorporated by reference. Meltblowing of KRATON copolymers ("KRATON" is a trade designation of the Shell Chemical Company) to form composite nonwoven elastic webs is described in U.S. Pat. No. 4,657,802 issued to Morman on Apr. 14, 1987 and titled "Composite Nonwoven Elastic Web", the disclosure of which is hereby incorporated by reference.

The elastic inner layer 20 and the outer layer 80, when desirable, may also be formed from elastically stretchable laminate materials. U.S. Pat. No. 4,657,802 to Morman also describes composite nonwoven elastic webs, such as spunbond laminate (hereinafter "SBL") webs. Other elastically stretchable laminate materials include NBL materials as are described in U.S. Pat. No. 5,226,992 issued on Jul. 13, 1993 to Morman, the disclosure of which is hereby incorporated by reference. Additionally, suitable breathable elastic film laminates are described in Provisional U.S. Patent Application Ser. No. 60/518,100 filed on Nov. 7, 2003 and titled "Microporous Breathable Elastic Film Laminates, Methods of Making Same, and Limited Use or Disposable Product Applications", the disclosure of which is hereby incorporated by reference. Further, suitable elastic laminates are also described in a U.S. patent application Ser. No. 10/743,25 filed on Dec. 22, 2003 and titled "Extensible and Stretch Laminates and Method of Making Same" having attorney reference number "K-C 20,006", the disclosure of which is hereby incorporated by reference.

The elastic inner layer 20, suitably presents a bodyfacing surface 23 that is compliant, soft feeling, and nonirritating to the wearer's skin. Further, the elastic inner layer 20 may be liquid permeable or liquid impermeable. When the elastic inner layer 20 is liquid permeable, the elastic inner layer 20 may be sufficiently porous to permit liquid to readily penetrate through the thickness of the elastic inner layer 20. Desirably, the elastic inner layer 20 presents a relatively dry surface to the wearer of the disposable garment 100. In order for the elastic inner layer 20 to be liquid impermeable, the elastic inner layer 20 may be composed of a substantially hydrophobic material. The hydrophobic material may optionally be treated with a surfactant or otherwise processed to impart a desired level of wettability and hydrophilicity. The material used to form the elastic inner layer 20 may be surface treated with about 0.3 weight percent of a surfactant, such as a surfactant commercially available from Hodgson Textile Chemicals, Inc. under the trade designation AHCOVEL Base N-62. The surfactant may be applied by any conventional means, such as spraying, printing, brush coating or similar techniques. The surfactant may be applied to the entire elastic inner layer 20 or may be selectively applied to particular sections of the elastic inner layer 20, such as the medial section along the longitudinal centerline of the disposable garment 100, to provide greater wettability of such sections. The elastic inner layer 20 may further include a lotion or treatment applied thereto that is configured to be transferred to the wearer's skin. Suitable compositions for application to the elastic inner layer 20 are described in U.S. Pat. No. 6,149,934 that issued to Krzysik et al. on Nov. 21, 2000, the disclosure of which is hereby incorporated by reference.

The elastic inner layer 20 may define an opening 90 where the opening 90 may be located in an internal position to the perimeter 25 of the elastic inner layer 20. The elastic inner layer perimeter 25 generally corresponds to the border defined by the elastic inner layer 20. The opening 90 may be in the form of a slit or an aperture. The size of the opening 90 may be varied depending on the size of the disposable garment 100 and the intended functions of the elastic inner layer 20. The opening 90 may be described in terms of its length relative to the total length 120 of the disposable garment 100 in the longitudinal direction 60. For example, the length 95 of the opening 90 may be from about 10% to about 90% of the total garment length 120. More specifically, the length 95 of the opening 90 may be from about 20% to about 70% of the total garment length 120. Alternatively, the length 95 of the opening 90 may be from about 30% to about 50% of the total garment length 120. As a specific example of a suitable length for an opening 90 of the invention, if the garment length 120 is 381 millimeters (mm), the length 95 of the opening 90 may range from 76 mm to 267 mm. In addition to its length 95, the opening 90 may be characterized by its location within the elastic inner layer 20. The opening 90 may be located near the lateral centerline (the midpoint of the garment's width in the lateral direction) in the crotch region 50 of the garment 100. The opening 90 may extend in the longitudinal direction 60 toward the perimeters of the front waist region 30 and the back waist region 40.

If the opening 90 is in the form of a slit, the slit may have a single straight cut or a cut with branches. For example, the opening 90 may include a slit formed in the elastic inner layer 20 at the center of the garment 100 and may further include additional "branch" slits extending away from the "tails" of the center slit. The "branch" slits may be formed at various angles to the center slit. The opening 90 may also be in the form of an aperture. The aperture, unlike the slit, may form an area in the inner elastic layer 20 through which the outer layer may be visible. The aperture may be characterized by its area; for example, the area of the aperture may range from about 5% to about 25% of the total surface area for the elastic inner layer 20. More specifically, the surface area of the aperture may range from about 7% to about 19% of the total surface area. Alternatively, the surface area may be from 10% to about 14% of the total surface area. A specific example of an aperture that would be suitable to form an opening 90 of the invention includes a garment 100 having a length 120 of 381 mm, front and back waist region widths of 241 mm and a crotch width of 75 mm to provide a total surface area for the elastic inner layer 20 of 3015 $mm^2$. The area of the aperture may range from about 101 $mm^2$ to about 508 $mm^2$. The aperture may also be described in terms of its width. The width of the aperture may range from about 13 mm to about 101 mm. More specifically, the width of the aperture may range from about 25 mm to about 76 mm. The aperture may also be described in terms of its shape. For example, the elastic inner layer 20 may have an opening 90 in the shape of an hourglass, a rectangle or a trapezoid.

Just as the size of the opening 90 may be related to the elastic inner layer 20 in terms of surface area, the size of the elastic inner layer 20 relative to the outer layer 80 may be considered in terms of surface area. For example, the elastic inner layer 20 may have a smaller surface area than the outer layer 80. As surface area is determined by length and width, the outer layer 80 may have a greater length in the longitudinal direction 60 of the disposable garment 100 than the elastic inner layer 20. The length of the elastic inner layer 20 may be determined when the elastic inner layer 20 is in a relaxed and retracted state. The outer layer 80 may also have a width in the lateral direction 70 that is greater than the width of the elastic inner layer 20 in the lateral direction 70. When the garment 100 is constructed so that the elastic inner layer 20 is smaller than the outer layer 80 in its relaxed, retracted state, the elastic inner layer 20 provides a snug fit against the body of the wearer of the garment 100 while the larger, outer layer 80 provides area and volume for containment.

Figure 5:
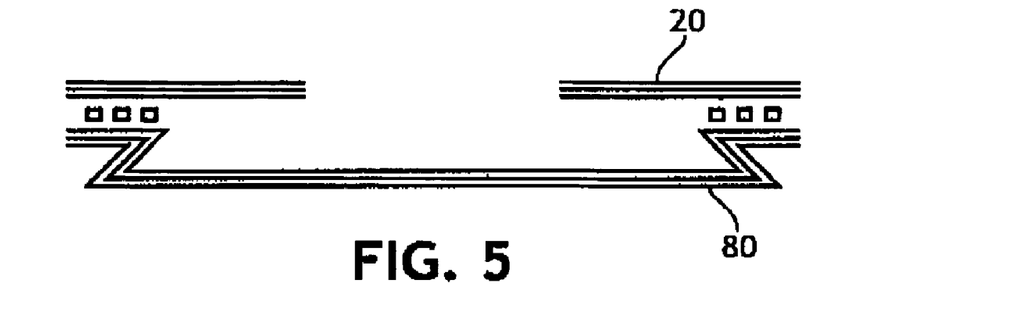
FIG. 5 representatively shows a cross-section of the crotch region of a disposable garment such as the one shown in FIG. 1.
Figure 6:
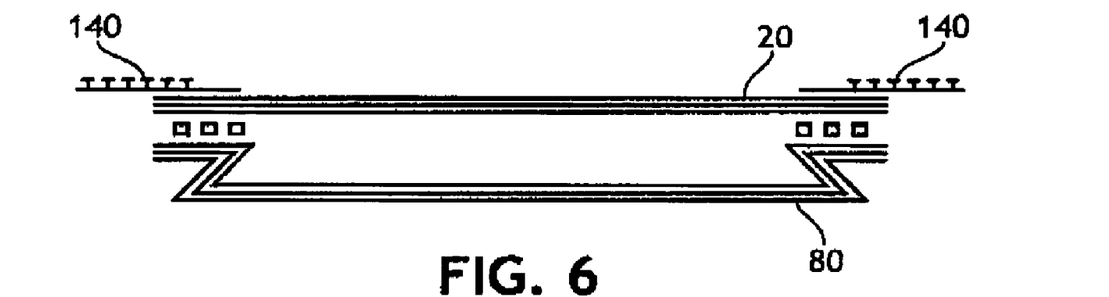
FIG. 6 representatively shows a cross-section of the back waist region of a disposable garment such as the one shown in FIG. 1.

There are several approaches for providing a garment 100 having an elastic inner layer 20 that is smaller than the outer layer 80. For example, the elastic inner layer 20 may be stretched or elongated during manufacture and then attached to an outer layer 80 formed of non-stretchable material. The layers may be attached to each other using known bonding techniques such as adhesive, ultrasonic or thermal bonding. The elastic inner layer perimeter 25 may be attached to the outer layer 80. The elastic inner layer perimeter 25 may be "matched" up with the outer layer perimeter 85 or the elastic inner layer perimeter 25 may be attached to the outer layer 80 within the outer layer perimeter 85. After the elastic inner layer 20 and the outer layer 80 are bonded together, the elongated elastic inner layer 20 retracts and gathers the outer layer 80. As a result, the gathered outer layer 80 may appear blousy. FIG. 5 representatively shows a cross-section of the crotch region 50 of the garment 100 shown in FIG. 1 after an elastic inner layer 20 was elongated, the elastic inner layer perimeter 25 was bonded to the outer layer perimeter 85 and the garment 100 was allowed to relax. FIG. 5 shows the gathered outer layer 80 having a greater width than the elastic inner layer 20. FIG. 6 representatively shows a cross-section of the back waist region 40 of the garment 100 shown in FIG. 1 in which fasteners 140 are provided near the longitudinal side edge 55 (or garment perimeter 110) of the elastic inner layer 20. The fasteners 140 may be used to join the back waist region 40 with the front waist region 30 when the garment 100 is donned. The fasteners 140 may be provided on the bodyfacing surface 23 of the elastic inner layer 20. The bodyfacing surface 23 is the surface of the elastic inner layer 20 that comes into contact with the wearer's skin. The fasteners 140 may be provided near the longitudinal side edge 55 of the garment 100 and near where the elastic inner layer perimeter 25 is bonded to the outer layer 80. Positioning the fasteners 140 in this location provides for the smaller elastic inner layer 20 to stretch before the outer layer 80 during application and as a result, the elastic inner layer 20 may snuggly fit to the body.

As described herein, the elastic inner layer 20 may be provided by a material that has multi-directional stretch. When the elastic inner layer 20 is stretched in more than one direction prior to bonding with the outer layer 80, the resulting garment 100 has an outer layer 80 that has been gathered in more than one direction. A gathered perimeter 110 may be formed by the elongated elastic inner layer 20 being bonded-to the non-stretchable outer layer 80. This construction provides the advantage of an outer layer 80 that may be gathered in any shape or surface area needed for a particular disposable garment design. This construction also provides the ability to form a garment 100 having areas of curvature (e.g. highly curved gatherings) without the need to incorporate individual, highly-curved elastic components.

The degree to which the outer layer 80 is gathered is related to the elongation and stretch direction of the elastic inner layer 20. When the elastic inner layer perimeter 25 is bonded to the outer layer 80, the direction of stretch of the elastic inner layer 20 will create gathers. The elastic inner layer 20 may be constructed of elastic materials that are capable of providing a range of tension and percent elongation. For example, the material may have percent elongation of from about 10% to about 400%. More specifically, the percent elongation may range from about 30% to about 200% or from about 50% to about 150%. The percent elongation may be different in different directions of stretch. For example, a suitable elastic material for constructing the elastic inner layer 20 may have a percent elongation of 50% in the cross-direction (or lateral direction 70) and a percent elongation of 100% in the machine direction (or longitudinal direction 60). Suitable elastic materials may also be characterized by the force to elongate the material and the retractive force that the material provides during use. For example, the force to elongate may range from about 100 grams to about 1000 grams (based on elongating a 7.62 centimeter (cm) wide sample to 50% elongation). More specifically, the force to elongate may range from about 200 grams to about 800 grams or from about 400 grams to about 600 grams. The retractive force provided during use may be similar to the force to elongate.

Figure 7:
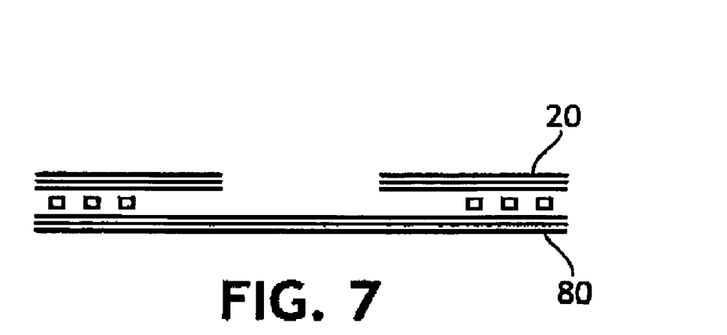
FIG. 7 representatively shows a cross-section of the crotch region of a disposable garment such as the one shown in FIG. 1 before the garment is donned and where the outer layer is formed from an extensible material.
Figure 8:
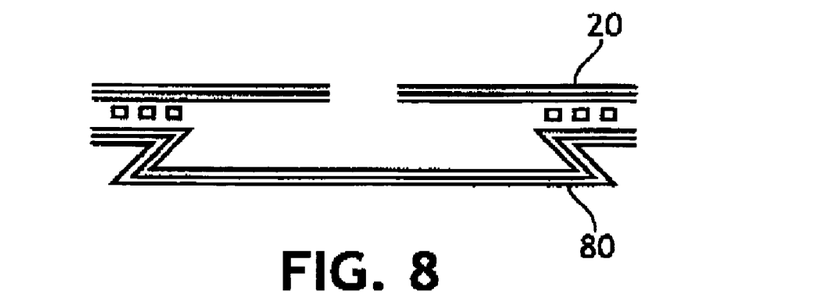
FIG. 8 representatively shows a cross-section of the crotch region of a disposable garment such as the one shown in FIG. 1 after the garment is donned and where the outer layer is formed from an extensible material.

Another approach for providing a garment 100 having an elastic inner layer 20 that is smaller than the outer layer 80 is to provide an outer layer 80 formed from an extensible material. The extensible material may be capable of extending in a machine direction (e.g. longitudinal direction 60) and/or a cross-direction (e.g. lateral direction 70). Extensible materials are capable of increasing their length in a given direction and therefore, their area, with minimal force. The percent extensibility of a material may be defined as the difference between the extended surface area and the initial surface area divided by the initial surface area; the quotient then being multiplied by 100. With a multi-directional extensible material, the material may increase its length in multiple directions and therefore, increase the surface area of the outer layer 80 to a degree related to the percent extensibility of the material. For example, the percent extensibility of a suitable material may range from about 10% to about 150%. More specifically, the percent extensibility may range from about 20% to about 80% or from about 30% to about 50%. Suitable materials for forming an extensible outer layer 80 are described in U.S. Pat. No. 6,610,383 entitled "Transversely Extensible and Retractable Necked Laminate of Non-Elastic Sheet Layers" which issued on Aug. 26, 2003 to Morman et al. and U.S. Pat. No. 6,632,212 entitled "Breathable Laminate Permanently Conformable to the Contours of A Wearer" which issued on Oct. 14, 2003 to Morman et al., the disclosures of which are hereby incorporated by reference. An advantage of this approach is that the elastic inner layer 20 does not have to be elongated prior to bonding to the outer layer 80. Another difference is that bonded region 115 may not have a gathered appearance prior to the garment 100 being worn. When the garment 100 is stretched during donning, the outer layer 80 formed with an extensible material will elongate, thereby increasing its area and creating a gathered appearance where the elastic inner layer perimeter 25 is bonded. This aspect is representatively illustrated in FIG. 7 and FIG. 8. FIG. 7 representatively shows a cross-section of a disposable garment such as that shown in FIG. 1 in which the outer layer 80 is formed from an extensible material, prior to the garment being donned. In FIG. 7, the length of the outer layer 80 is the same as the length of the elastic inner layer 20. FIG. 8 representatively shows the same cross-section as FIG. 7, but after the garment has been stretched, such as during donning. In FIG. 8, the length of the outer layer 80 is greater than the length of the elastic inner layer 20.

Yet another approach to providing a garment 100 having an elastic inner layer 20 that is smaller than the outer layer 80 is to use an outer layer 80 that has a three-dimensional shape. As with the previous approach, an advantage of this approach is that the elastic inner layer 20 does not have to be elongated prior to bonding with the outer layer 80. An example of an outer layer 80 having a three-dimensional shape is to provide an outer layer 80 that has one or more pleats. The pleats permit an outer layer 80 having a length that is greater than the length of an attached elastic inner layer 20 in the cross-direction of the garment 100.

As already described herein, the disposable garments 100 of the invention are constructed in such a way that the elastic inner layer perimeter 25 is bonded to the outer layer 80. The elastic inner layer perimeter 25 may be bonded by using bonding techniques such as adhesive, ultrasonic or thermal bonds. In one aspect, the elastic inner layer perimeter 25 is bonded to the outer layer perimeter 85. The perimeter bonding of the components permits the elastic inner layer 20 to fully stretch. Additionally, as already described, when the elastic inner layer 20 is bonded to an outer layer 80 formed of a non-stretchable material, the perimeter bonding creates the visual appearance of gathered waist and leg regions without the addition of separate elastic components, such as waistbands and leg elastics. Elimination of the need to incorporate separate elastic components results in a garment 100 that lies flat. This feature is significant when the garment 100 is in the form of an infant diaper; diapers that lie flat are easier to apply to infants and toddlers than diapers that want to curl closed. Additionally, the perimeter bonding provides an elastic inner layer retraction value that is greater than an outer layer retraction value. Desirably, the elastic inner layer retraction value is greater than the outer layer retraction value regardless of the type of material from which the outer layer 80 is made. If the outer layer 80 is made from a non-stretchable material, the elastic inner layer retraction value will be inherently greater (because the material of the outer layer 80 has no significant retraction). If the outer layer 80 is made from an extensible material or an elastic material, the retractive force of that material is desirably less than the retractive force of the material used to form the elastic inner layer 20.

The perimeter bonding that is used to form garments 100 of the invention may have several characteristics. For example, one characteristic is the percent of the perimeter of the elastic inner layer 20 that is bonded to the outer layer 80. In FIGS. 1-4, 100% of the elastic inner layer perimeter 25 is shown as being bonded to the outer layer perimeter 85. However, it is not necessary for the entire elastic inner layer perimeter 25 to be bonded to the outer layer 80. The disposable garments 100 of the invention may have about 60% of the elastic inner layer perimeter 25 bonded to the outer layer 80, including the outer layer perimeter 85. Likewise, about 80% of the elastic inner layer perimeter 25 may be bonded to the outer layer 80. The greater the percentage of the elastic inner layer perimeter 25 that is bonded to the outer layer 80, the better the elastic inner layer 20 controls the outer layer 80 during use. Another characteristic of the perimeter bonding is the percentage of bonded area, which may also be understood to represent the density of the bond pattern. The percentage of bonded area may be determined by measuring the bonded area, subtracting the area of the actual bonds, dividing the difference by the bonded area and multiplying by 100 to obtain the percentage of the bonded area that is not bonded. This percentage may then be subtracted from 100 to provide the percentage of bonded area. The percentage of bonded area may range from about 3% to about 70%. More specifically, the percentage of bonded area may range from about 7% to about 30% or from about 10% to about 20%. The perimeter bond may also be characterized by its width. Along the longitudinal side edges 55 of the garment 100, the width of the perimeter bond 115 would be in a direction generally perpendicular to the longitudinal direction 60 of the garment 100. Along the waist edges 35 and 45 of the garment 100, the width of the perimeter bond 115 would be in a direction generally perpendicular to the lateral direction 70 of the garment 100. The width of the perimeter bond 115 may range from about 3 mm to about 50 mm. More specifically, the width of the perimeter bond 115 may range from about 6 mm to about 25 mm or from about 12 mm to about 19 mm. Another characteristic of the perimeter bond 115 is the location of the perimeter bond. The location of where the elastic inner layer perimeter 25 is bonded to the outer layer 80 may be next to or adjacent the garment perimeter 110. For example, an outward edge of the elastic inner layer perimeter 25 may be located within about 5 mm to about 25 mm from the garment perimeter 110.

The elastic inner layer perimeter 25 may be bonded to the outer layer 80, including the outer layer perimeter 85, using various techniques. As already described, the elastic inner layer perimeter 25 may be ultrasonically bonded to the outer layer 80. The shape of the bonding pattern may include a pattern anvil roll that takes the shape of the perimeter being bonded. An advantage of this method is that the bond pattern may also include a raised edge that permits the anvil roll to bond the two or more layers of materials, but also trims excess material that extends outward beyond the perimeter bond 115. The perimeter of the garment 100 may also be bonded with the use of pressure and heat. The shape of the bond pattern would be a pattern anvil roll and when the composite is run through the nip, the composite would be pressure bonded to the shape of the bond pattern. Additionally, the perimeter 110 of the garment 100 may also be bonded with the use of adhesive. Desirably, the adhesive may be applied in a pattern that outlines the perimeter 110 of the garment 100. The adhesives may be of a pressure-sensitive type or of a type that may be applied as a print adhesive.

Figure 10:
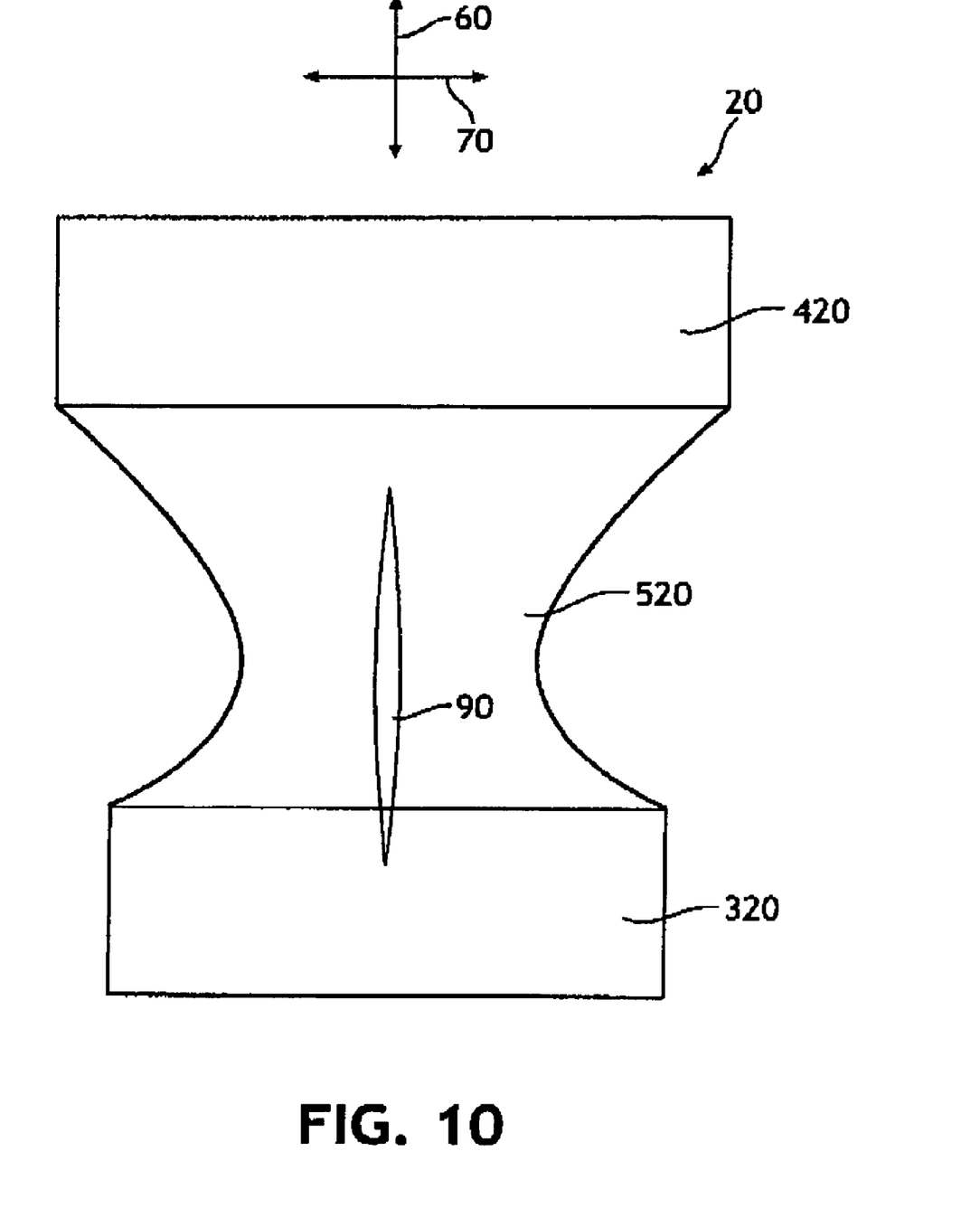
FIG. 10 representatively shows a plan view of an elastic inner layer having more than one section that may be used with the disposable garments of the invention.

The disposable garments 100 of the invention may be constructed of an elastic inner layer 20 that is not continuous and is constructed of two or more pieces. A multiple piece construction of the elastic inner layer 20 creates the opportunity to provide garments 100 having stretch characteristics that are tailored for the various regions of the garments 100. For example, an elastic inner layer 20 may be provided that has a front waist region 30, a back waist region 40 and a crotch region 50 being elastically stretchable in different directions. FIG. 10 representatively illustrates an elastic inner layer 20 of the invention that includes a front piece 320, a back piece 420 and a crotch piece 520. In a particular combination, the front piece 320 and the back piece 420 may be elastic in the lateral direction 70 while the crotch piece 520 is elastic in the longitudinal direction 60. The front piece 320 and the back piece 420 may be attached to the crotch piece 520 using adhesives or ultrasonic or thermal bonding. Alternatively, the crotch piece 520 may be elastic in the longitudinal direction 60 and extensible in the lateral direction 70. Other combinations are also possible. For example, the front piece 320 may be elastic in the lateral direction 70 while the back piece 420 and the crotch piece 520 are elastic in both the lateral direction 70 and the longitudinal direction 60. The opening 90 may be formed within only the crotch piece 520 or alternatively, the opening 90 may extend between the front piece 320, the back piece 420 and the crotch piece 520. Desirably, the crotch piece 520 has a greater retraction value than the outer layer 80. When the crotch piece 520 has a greater retraction value than the outer layer 80, the outer layer 80 has a greater surface area in the crotch region 50 while maintaining the surface area of the front and back waist regions 30 and 40, respectively.

Figure 9:
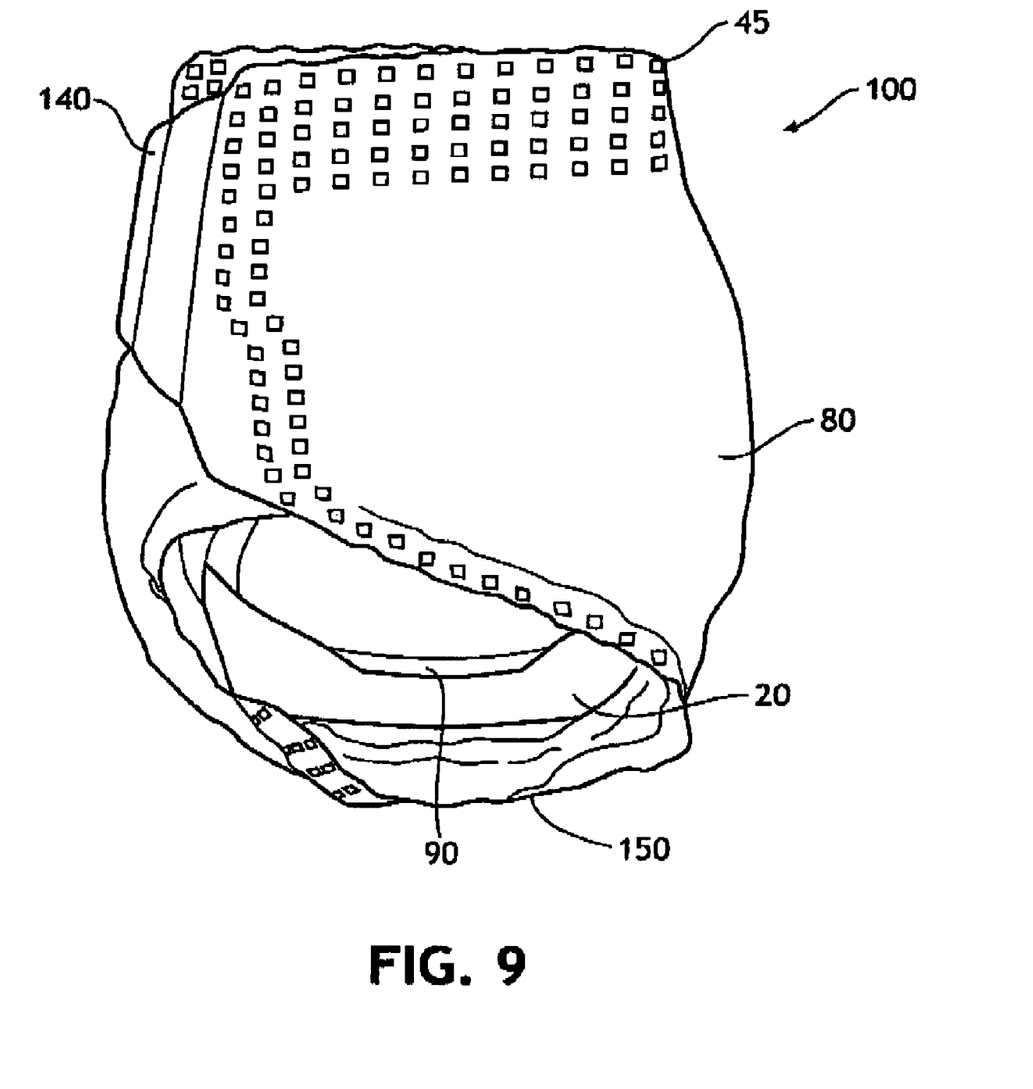
FIG. 9 representatively shows a side view of a disposable absorbent garment of the invention as the garment would look during wear and after loading with waste fluids.

The close-to-the-body fit of the disposable garments 100 of the invention may be provided in part, by the combination of the elastic inner layer 20 and the perimeter bonding of the elastic inner layer perimeter 25 to the outer layer 80. The capacity of the disposable garments of the invention to contain bodily wastes may be provided by the combination of the opening 90 together with the manner in which the elastic inner layer 20 is attached to the outer layer 80. When all of the features are combined, the disposable garments 100 of the invention unexpectedly provide excellent fit, minimal leakage and a simple garment construction that does not require the attachment of many individual components. The present invention also relates to disposable absorbent garments 100. The disposable absorbent garments may include an elastic inner layer 20, an outer layer 80 and may also include an absorbent assembly 150 that is positioned between the outer layer 80 and the elastic inner layer 20. FIG. 9 representatively illustrates a side view of a disposable absorbent garment 100 of the invention after the garment has absorbed waste fluids. As shown, the elastic inner layer 20 remains in position, close to the body of the wearer, while the outer layer 80 and the absorbent assembly 150 move outward. Consequently, the absorbent assembly 150 holding the waste fluids is separated from the wearer's skin. The absorbent assembly 150 may include a topsheet layer, a core layer and a barrier layer.

The topsheet layer of the absorbent assembly 150 may define a bodyfacing surface that is compliant, soft feeling, and nonirritating to the wearer's skin. Further, the topsheet layer may be less hydrophilic than the core layer. The topsheet layer may be formed from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. Various woven and nonwoven fabrics may be used for the topsheet layer. For example, the topsheet layer may be formed of a meltblown or spunbond web of polyolefin fibers. The topsheet layer may also be a bonded-carded web composed of natural and/or synthetic fibers. The topsheet layer may be composed of a substantially hydrophobic material, and the hydrophobic material may, optionally, be treated with a surfactant or otherwise processed to impart a desired level of wettability and hydrophilicity. For example, the topsheet layer may include a nonwoven, spunbond, polypropylene fabric composed of about 2.8-3.2 denier fibers formed into a web having a basis weight of about 22 grams per square meter and a density of about 0.06 gram per cubic centimeter.

The core layer of the absorbent assembly 150 may suitably include a matrix of hydrophilic fibers, such as a web of cellulosic fluff, mixed with particles of a high-absorbency material commonly known as superabsorbent material. For example, the core layer may include a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be nonuniformly mixed. Alternatively, the core layer may include a laminate of fibrous webs and superabsorbent material or other suitable matrix for maintaining a superabsorbent material in a localized area. The size and the absorbent capacity of core layer should be compatible with the size of the intended wearer and the liquid loading imparted by the intended use of the disposable absorbent garment 100. Further, the size and the absorbent capacity of the core layer can be varied to accommodate wearers ranging from infants through adults.

The high-absorbency material may be selected from natural, synthetic, and modified natural polymers and materials. The high-absorbency materials may be inorganic materials, such as silica gels, or organic compounds, such as crosslinked polymers. The term "crosslinked" refers to methods for effectively rendering normally water-soluble materials substantially water insoluble but swellable. Such methods include, for example, physical entanglement, crystalline domains, covalent bonds, ionic complexes and associations, hydrophilic associations such as hydrogen bonding, and hydrophobic associations or Van der Waals forces. Examples of synthetic, polymeric, high-absorbency materials include the alkali metal and ammonium salts of poly (acrylic acid) and poly(methacrylic acid), poly(acrylamides), poly(vinyl ethers), maleic anhydride copolymers with vinyl ethers and alpha-olefins, poly(vinyl pyrrolidone), poly(vinyl morpholinone), poly(vinyl alcohol), and mixtures and copolymers thereof. Further polymers suitable for use in the core layer include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum, and the like. Mixtures of natural and wholly or partially synthetic absorbent polymers may also be useful. The high absorbency material may be in any of a wide variety of geometric forms. As a general rule, the high absorbency material is in the form of discrete particles. However, the high absorbency material may also be in the form of fibers, flakes, rods, spheres, needles, or the like. In general, the high absorbency material is present in the core layer in an amount of from about 5 to about 90 percent by weight, desirably in an amount of at least about 30 percent by weight, and even more desirably in an amount of at least about 50 percent by weight based on a total weight of the core layer. For example, in a particular aspect, the core layer may include a laminate which includes at least about 50 percent by weight and desirably at least about 70 percent by weight of high-absorbency material overwrapped by a fibrous web or other suitable material for maintaining the high-absorbency material in a localized area. An example of high-absorbency material suitable for use in the present invention is DRYTECH 2035 polymer available from Dow Chemical, a business having offices in Midland, Mich. Other suitable superabsorbents may include FAVOR SXM 880 polymer obtained from Stockhausen, a business having offices in Greensboro, N.C.

The barrier layer may be formed from a thin plastic film or other flexible liquid-impermeable material. For example, the barrier layer may be formed from a polyethylene film having a thickness of from about 0.013 millimeter (0.5 mil) to about 0.051 millimeter (2.0 mils). The barrier layer may also be formed from a polyolefin film having a nonwoven web laminated to the exterior surface thereof, such as a spunbond web of polyolefin fibers. For example, a stretch-thinned polypropylene film having a thickness of about 0.015 millimeter (0.6 mil) may be thermally laminated thereto a spunbond web of polypropylene fibers. The polypropylene fibers may have a fiber diameter of about 15 to 20 microns, which nonwoven web has a basis weight of about 17 grams per square meter (0.5 ounce per square yard). The barrier layer may include bicomponent fibers such as polyethylene/polypropylene bicomponent fibers. The barrier layer may also include a vapor permeable non-woven facing layer laminated to a micro-porous film to impart "breathability" to the barrier layer. Suitable "breathable" barrier layer materials are described in U.S. Pat. No. 5,695,868 issued Dec. 9, 1997 to McCormack et al. and U.S. Pat. No. 5,843,056 issued Dec. 1, 1998 to Good et al., the descriptions of which are hereby incorporated by reference.

The absorbent assembly 150 may be attached to the outer layer 80 of the disposable absorbent garment 100 using techniques known to those of skill in the art, such as adhesive attachment. For example, the length of the absorbent assembly 150 may be generally aligned with the length 120 of the garment 100 in the longitudinal direction 60. The absorbent assembly 150 may be attached to the outer layer 80 by adhesive running the length of the absorbent assembly 150 and located generally at the center of the width of the absorbent assembly. The width of the absorbent assembly 150 in a lateral direction 70 of the garment 100 may be divided in half by a lateral centerline. The placement of the adhesive may be targeted for the lateral centerline of the absorbent assembly 150.

Figure 2:
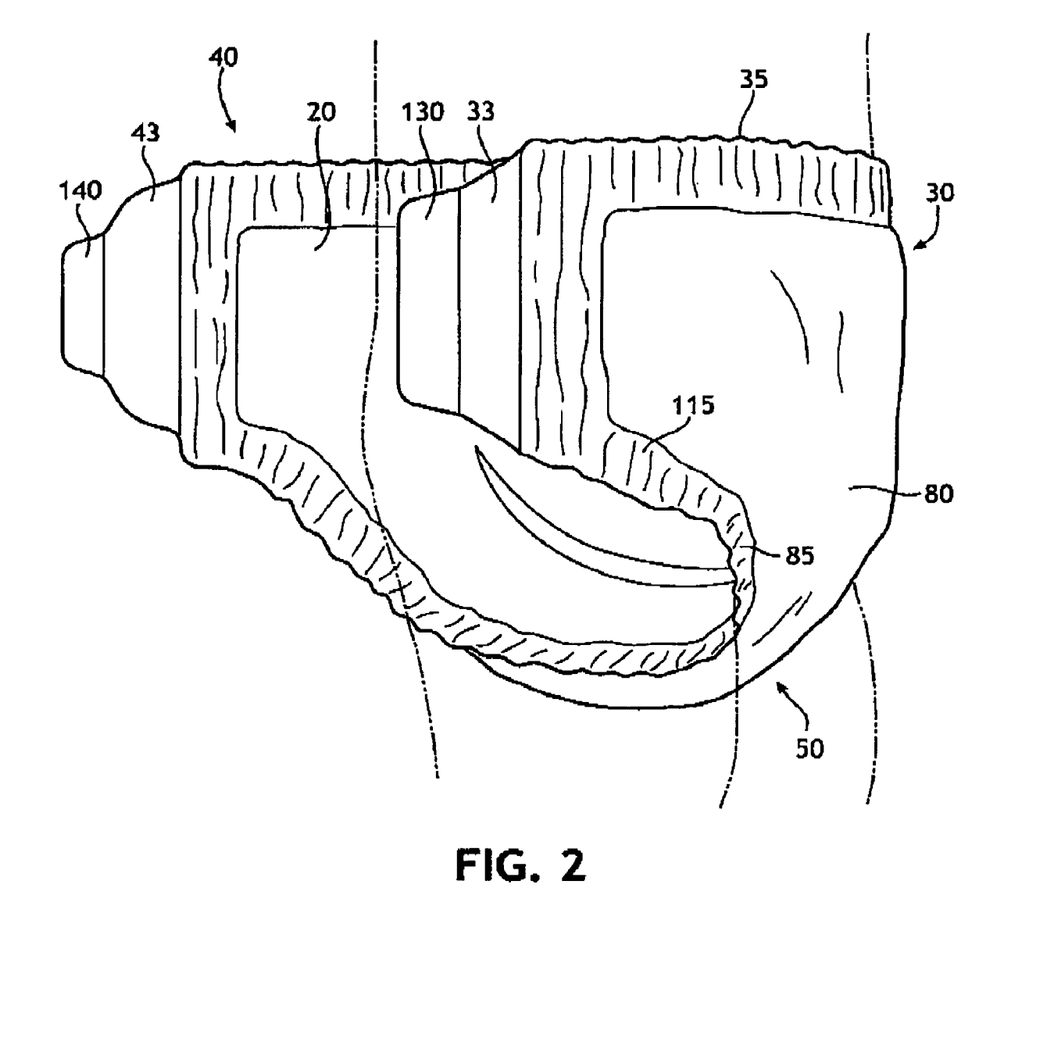
FIG. 2 representatively shows a perspective view of the disposable garment of FIG. 1 as it would be applied to a wearer (prior to fasteners being attached)
Figure 3:
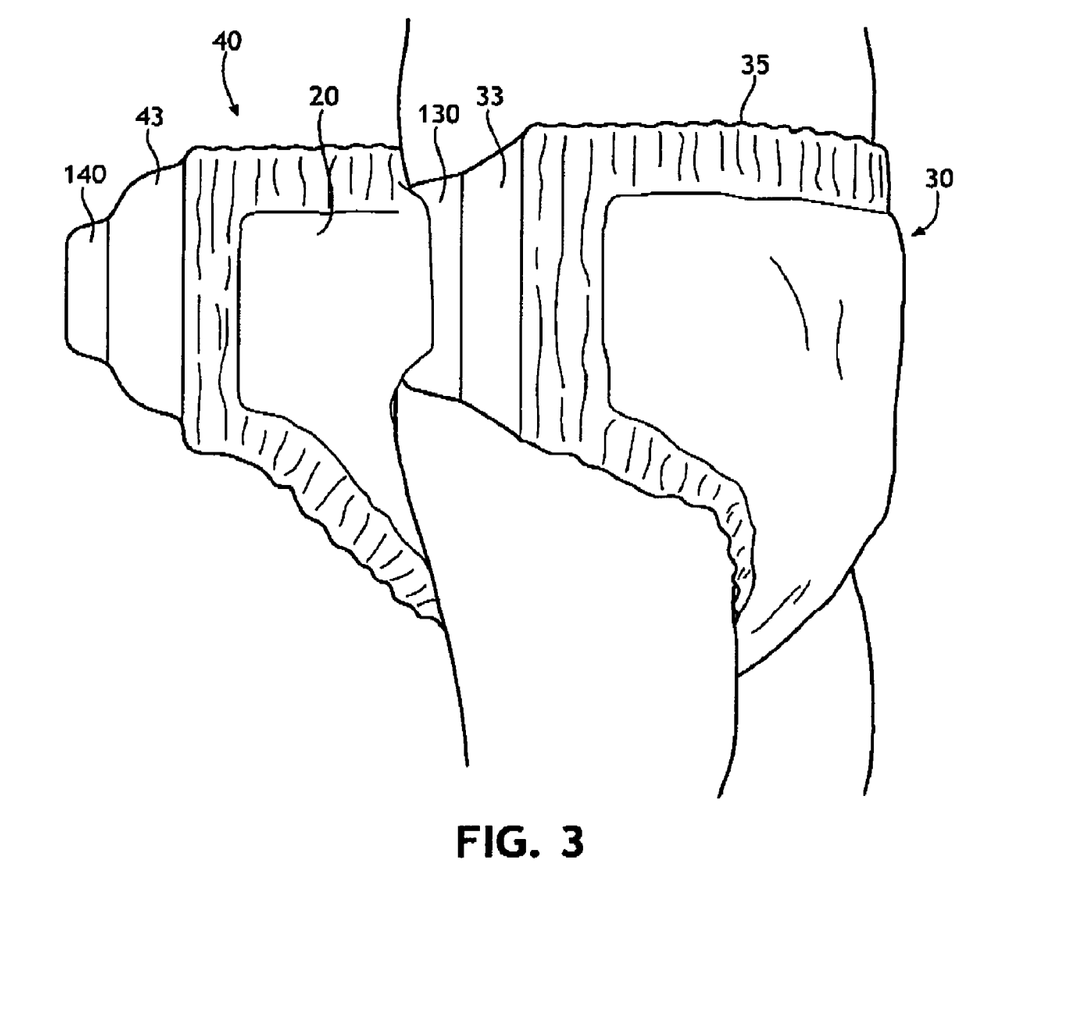
FIG. 3 representatively shows a perspective view of the disposable garment of FIG. 1 with a fastener being attached to the elastic inner layer.
Figure 4:
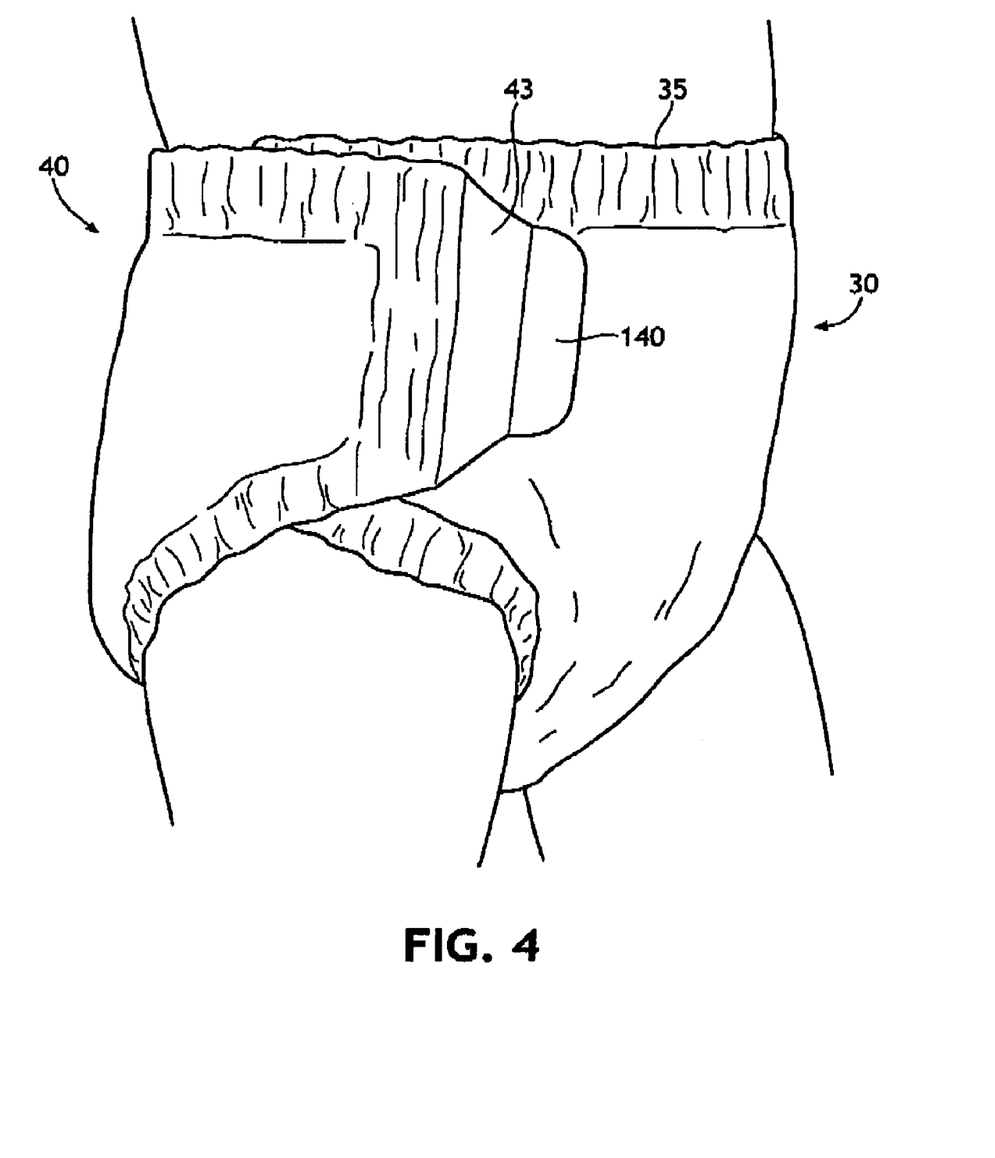
FIG. 4 representatively shows a perspective view of the disposable garment of FIG. 1 with a fastener being attached to the outer layer.

The disposable garments 100 and disposable absorbent garments 100 of the invention may include mechanical fasteners 130 and 140 for attaching the front waist region 30 and the back waist region 40 together. The material forming the mechanical fasteners 130 and 140 may be integral with the elastic inner layer 20 and the outer layer 80, or the material may be provided on separate portions (e.g. front ear portion 33 and back ear portion 43, both shown in FIG. 2) that are attached to the longitudinal side edges 55 of the garments 100 in the waist regions. In FIGS. 1-4 and in FIG. 9, the mechanical fasteners 130 and 140 are provided on separate portions that are attached to the garment 100 in the areas of the perimeter bond 115. The mechanical fasteners 130 and 140 may include a variety of materials and surfaces known for mechanical engagement such as buttons, pins, snaps, adhesive tape fasteners, cohesives, mushroom-and-loop fasteners and hook and loop fasteners. FIGS. 2-4 representatively illustrate how the mechanical fasteners 130 and 140 may be positioned to join the front waist region 30 and the back waist region 40. FIG. 2 illustrates the appearance of the mechanical fasteners 130 and 140 prior to engagement; FIG. 3 illustrates the engagement of mechanical fastener 130 into the elastic inner layer 20 of the garment 100 in the back waist region 40; and FIG. 4 illustrates how mechanical fastener 140 may be brought in overlapping relationship with mechanical fastener 130 for engagement into the outer layer 80 of the garment 100 in the front waist region 30.

The combination of structural features encompassed by the disposable garments and disposable absorbent garments of the invention provides a quality of fit and proper containment not previously attainable. For example, the combination of the elastic inner layer 20 and the bonding of the elastic inner layer perimeter 25 to the outer layer 80 provide garments having the volume to contain wastes while separating the wearer's skin from the wastes. These garments have improved simplicity and efficiency of manufacture because they do require the incorporation of many individual components. The perimeter bond 115 provides a gasket in the leg openings and waist opening of the garments 100 without the need for separately attached waistbands or leg elastics. Given the trend toward more complex disposable garments having more features and more components, the effectiveness of the garments 100 of the invention is unexpected.

While the disposable garments and disposable absorbent garments of the invention have been described in detail with respect to specific aspects thereof, it will be appreciated that those skilled in the art, upon attaining an understanding of the foregoing, may readily conceive of alterations to, variations of and equivalents to these garments. Accordingly, the scope of the present invention should be assessed as that of the appended claims and any equivalents thereto.

We claim:

1. A disposable absorbent garment, the disposable absorbent garment comprising:
    an outer layer;
    an elastic inner layer, wherein the elastic inner layer has an elastic inner layer perimeter;
    wherein the elastic inner layer includes a front piece, a back piece and a crotch piece, wherein the crotch piece is attached to the front piece and the back piece and wherein the front piece is elastic in a lateral direction and the back piece is elastic only in the lateral direction of the disposable absorbent garment and the crotch piece is elastic only in a longitudinal direction of the disposable absorbent garment;
    wherein the crotch piece defines an opening located in an internal position to the elastic inner layer perimeter;
    wherein the elastic inner layer perimeter is bonded to the outer layer; and
    an absorbent assembly positioned between the outer layer and the elastic inner layer, wherein the absorbent assembly includes a topsheet layer, a core layer and a barrier layer.

2. The disposable absorbent garment of claim 1, wherein the outer layer has an outer layer perimeter and the elastic inner layer perimeter is bonded to the outer layer perimeter.

3. The disposable absorbent garment of claim 1, wherein the outer layer is extensible.

4. The disposable absorbent garment of claim 1, wherein the outer layer is elastic.

5. The disposable absorbent garment of claim 1, wherein the outer layer is liquid impermeable.

6. The disposable absorbent garment of claim 1, wherein the outer layer is liquid permeable.

7. The disposable absorbent garment of claim 1, wherein the outer layer has one or more pleats.

8. The disposable absorbent garment of claim 1, wherein the elastic inner layer is liquid Impermeable.

9. The disposable absorbent garment of claim 1, wherein the elastic inner layer includes two or more layers of materials.

10. The disposable absorbent garment of claim 1, wherein the opening has a length of from 10% to 80% of a total length of the disposable absorbent garment.

11. The disposable absorbent garment of claim 1, wherein the elastic inner layer is bonded to the outer layer with a plurality of ultrasonic, adhesive or thermal bonds.

12. The disposable garment of claim 1, wherein the crotch piece is extensible in a lateral direction of the disposable garment.

13. The disposable absorbent garment of claim 1, wherein the outer layer has a length in the longitudinal direction, the elastic inner layer has a length in the longitudinal direction and the outer layer length is greater than the elastic inner layer length.

14. The disposable absorbent garment of claim 1, wherein the outer layer has a width in the lateral direction, the elastic inner layer has a width in the lateral direction and the outer layer width is greater than the elastic inner layer width.

15. The disposable absorbent garment of claim 1, wherein the disposable absorbent garment has a longitudinal side edge that includes a perimeter bonded area where the elastic inner layer is bonded to the outer layer, wherein the perimeter bonded area has a percentage of bonded area to unbonded area of from 10 to 40.

16. The disposable absorbent garment of claim 1, wherein the absorbent assembly is attached to the outer layer along a lateral centerline of the absorbent assembly.

* * * * *